United States Patent [19]
Morohashi

[11] 4,431,279
[45] Feb. 14, 1984

[54] EYE PERIPHERY PORTION ILLUMINATING DEVICE IN AN OPHTHALMOLOGIC INSTRUMENT

[75] Inventor: Kazuo Morohashi, Yokohama, Japan

[73] Assignee: Nippon Kogaku K.K., Tokyo, Japan

[21] Appl. No.: 299,386

[22] Filed: Sep. 4, 1981

[30] Foreign Application Priority Data

Sep. 22, 1980 [JP] Japan .................. 55-133686[U]

[51] Int. Cl.³ .............................................. A61B 3/00
[52] U.S. Cl. .................................... 351/245; 351/221
[58] Field of Search ............... 351/245, 221, 205, 211, 351/212

[56] References Cited

U.S. PATENT DOCUMENTS 3,545,846 12/1970 Wilms ............................. 351/212

Primary Examiner—John K. Corbin
Assistant Examiner—P. M. Dzierzynski
Attorney, Agent, or Firm—Shapiro and Shapiro

[57] ABSTRACT

In an eye periphery portion illuminating device in an ophthalmologic instrument having a chin supporting member and a forehead applying member for fixing a patient's face to the apparatus body, a downwardly open depression is formed in the forehead applying member and a light source is contained in the depression.

6 Claims, 4 Drawing Figures

EYE PERIPHERY PORTION ILLUMINATING DEVICE IN AN OPHTHALMOLOGIC INSTRUMENT

BACKGROUND OF THE INVENTION

1. Field of the Invention

This invention relates to an eye periphery portion illuminating device in an ophthalmologic instrument.

2. Description of the Prior Art

The conventional eye periphery portion illuminating device of this type has been provided in a portion of an ophthalomologic instrument body which faces a patient for the position adjustment of the patient's eyes and the apparatus body. The patient's face is fixed to the apparatus body by a chin supporting member and a forehead engaging member, and the ophthalmologic instrument body is moved so as to be position-adjusted to the illuminated patient's eyes. However, such an illuminating device has suffered from a disadvantage in that the image of the illuminating light is reflected from the patient's corneas.

Also, illumination by visible light leads to the problems that the patient feels dazzled and that the pupils become narrow. Illumination by infrared light may be effected through the use of a filter, but in such case the observation of the illuminated eye periphery portions cannot be accomplished by the use of the naked eye, and devices such as an image pick-up tube for infrared light and a TV monitor are required. Even then, the reflected images from the corneas appear on the TV monitor and often interfere with observation or measurement.

SUMMARY OF THE INVENTION

It is an object of the present invention to provide an eye periphery portion illuminating device in an ophthalmologic instrument which is capable of illuminating a patient's eye periphery portions without creating the reflected images from the corneas.

The invention will become fully apparent from the following detailed description of an embodiment thereof taken in conjunction with the accompanying drawings.

DESCRIPTION OF THE PREFERRED EMBODIMENT

Figure 4:
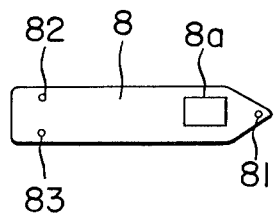
FIG. 4 is a plan view of a lid that may be employed in the invention.

As shown in the drawings, an ophthalmologic instrument having an eye periphery portion illuminating device according to an embodiment of the present invention may comprise a stand 1 having a pair of vertical struts 2a and 2b at the left and right sides of the stand. A beam 3 employed as the patient's chin supporting member and a beam 4 employed as the forehead engaging member extend horizontally between the struts 2a and 2b. A pad 3a on which the patient's chin may be laid is secured to the beam 3. The beam 3 is mounted to the struts 2a and 2b for vertical movement to determine the position of the patient's face. Left and right pads 4a and 4b against which the patient's forehead may bear are attached to the beam 4. The beam 4 is hollow and the underside thereof provides opening portions, thereby forming downwardly open depressions in which are provided left and right light sources 5a and 5b for illuminating the eye periphery portions. Lead wires 6a and 6b for supplying a current to the light sources 5a and 5b pass through the struts 2a and 2b and are connected to a power source, not shown, in the stand 1. Since the light sources 5a and 5b are adapted to be connected to the lead wires 6a and 6b through sockets 7a and 7b, replacement of the light sources 5a and 5b may be easily accomplished through the opening portions in the underside of the beam 4. The opening portions in the underside of the beam 4 are adapted to be closed separately from each other by lids 8 each having a window 8a as shown in FIG. 4. The left and right lids 8 are identical to each other and so, only the left one will be described herein. The left lid 8 is positioned so that if screws are threaded into threaded holes 41, 42 and 43 in the beam 4 from below the lid 8 with through-holes 81, 82 and 83 in the lid 8 registered with the threaded holes 41, 42 and 43, the window 8a will lie just under the light source 5a.

With such a construction, if a switch 1a on the stand 1 is closed to turn on the light sources 5a and 5b, the light beams from the light sources 5a and 5b will pass downwardly through the windows 8a of the lids 8 secured to the underside of the beam 4 and illuminate the eye peripheral portions of the patient. At this time, the illuminating light beams will illuminate the peripheral portions of the patient's eyes from slightly ahead of the patient's forehead and so, due to the interception effect of the patient's eyelids, there will be little or no light beam which will directly enter into the eyeballs. Accordingly, not only will the patient hardly feel dazzled in spite of his eye periphery portions being illuminated, but also the reflected images from the surface of the corneas resulting from the illumination of the eye periphery portions will become insignificant and thus, the influence imparted to the measurement by such reflections will be eliminated.

Figure 1:
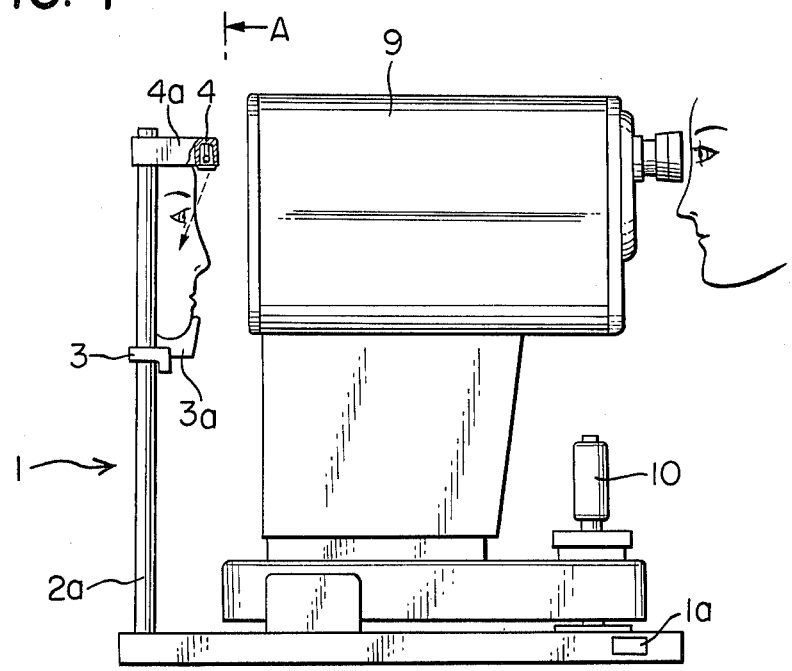
FIG. 1 is a partly cross-sectional side elevation view showing the use of an ophthalmologic instrument having an eye periphery portion illuminating device according to an embodiment of the present invention.
Figure 2:
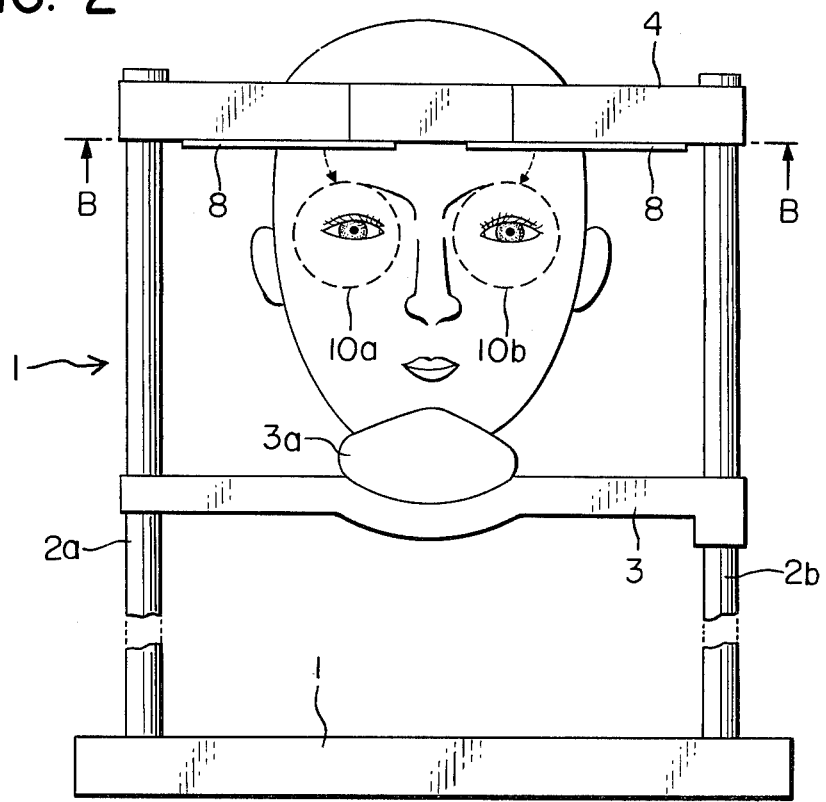
FIG. 2 is a front view taken along arrow A of FIG. 1.
Figure 3:
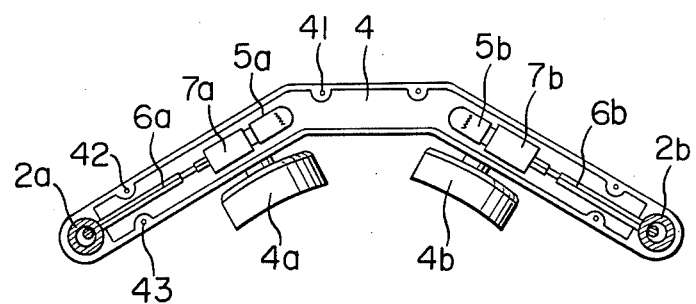
FIG. 3 is a bottom view taken along arrow B of FIG. 2.

The range of the illumination of the eye periphery portions when the ophthalmologic instrument body 9 has been moved by a joy stick 10 and the position adjustment of the patient's eyes to the ophthalmologic instrument body 9 has been completed is substantially the degree encircled by broken lines 10a and 10b of FIG. 2. That is, the spacing between the two light sources 5a and 5b is substantially equal to the spacing between the eyes of a human being (preferably an adult).

While in the above-described embodiment the beam 4 employed as the forehead applying member is formed of a member separate from the struts 2a and 2b, the beam 4 may also be a member integral with the struts 2a and 2b, namely, a part of a member such as a pipe bent into a U-shape. Also, in the above-described embodiment, the pads 4a and 4b against which the patient's forehead may bear are provided on the beam 4, but if a recess conformable to the configuration of the forehead is formed in the central portion of the beam 4, the pads 4a and 4b will be unnecessary. The lids 8 need not always be provided.

In the above-described embodiment, the power source for supplying a current to the light sources 5a and 5b is provided on the stand 1, whereas the location of the power source is not restricted thereto but, for example, a small battery may be incorporated into the beam 4.

According to the present invention, as described above, light sources are contained in the forehead engaging member usually used to fix the patient's forehead, and the eye periphery portions are illuminated from above the patient's eyes and therefore, the peripheral portions of the patient's eyes can be illuminated without the reflected images from the corneas being formed. Moreover, the present invention not only has an advantage in that there is no necessity of providing the eye periphery portion illuminating device in the ophthalmologic instrument body or of providing a separate illuminating portion holding mechanism, but also, in spite of the differences in construction between ophthalmologic instrument bodies which may exist depending on the elements to be measured, namely, the functions of the eyes to be measured, the present invention can provide illumination of the eye periphery portions under the same conditions.

Further, if the light sources of the present invention are chosen to provide infrared light, they will also be effective where an image pick-up tube for infrared light is used.

I claim:

1. An eye periphery portion illuminating device in an ophthalmologic instrument having a chin supporting member and a forehead engaging means for fixing a patient's face to the ophthalmologic instrument body, comprising:
   (a) beam means supporting said forehead engaging means; and
   (b) illuminating means for illuminating eye periphery portions of the patient's eyes, the illuminating means being disposed on said beam means so as to be positioned above the patient's face fixed as aforesaid and illuminating the periphery portions of the patient's eyes from slightly ahead of the patient's forehead so that, due to the interception effect of the patient's eyelids, little or no light will directly enter into the patient's eyeballs.

2. The device according to claim 1, wherein said beam means has downwardly open depressions in the vicinity of a part of said beam means supporting said forehead engaging means and having opening portions positioned to correspond in position to the eyes of the patient whose face is fixed as aforesaid, and wherein said illuminating means comprises a pair of light sources positioned in said depressions, respectively, the illuminating means illuminating said eye periphery portions through said opening portions.

3. The device according to claim 2, wherein said eye periphery portion illuminating device is provided with lid means formed with light interception portions for narrowing said opening portions, the lid means being removably mounted on said beam means, said light interception portions defining windows of size to illuminate the periphery portions of the patient's eyes.

4. The device according to claim 2, wherein said ophthalmologic instrument has a stand provided with two hollow struts which are spaced apart a predetermined distance from each other and which are provided substantially vertically on said stand, so that said struts may be positioned on opposite sides, respectively, of the face of the patient whose face is fixed as aforesaid, with said beam means substantially perpendicularly astride said two struts.

5. The device according to claim 4, wherein said illuminating means comprises lead wire means for supplying energy to said light sources, said lead wire means passing through hollow strut portions.

6. The device according to claim 2, wherein said forehead engaging means has a pair of pads; and said depressions are formed in said beam means in the vicinity of portions of the beam means supporting said pads, respectively.

* * * * *